United States Patent
Stierstorfer et al.

(10) Patent No.: US 11,666,301 B2
(45) Date of Patent: Jun. 6, 2023

(54) DATA CORRECTION IN X-RAY IMAGING

(71) Applicant: Siemens Healthcare GmbH, Erlangen (DE)

(72) Inventors: Karl Stierstorfer, Erlangen (DE); Martin Petersilka, Adelsdorf (DE); Martin Hupfer, Erlangen (DE); Achim Hillenbrand, Erlangen (DE); Matthias Baer-Beck, Erlangen (DE); Rainer Raupach, Heroldsbach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 315 days.

(21) Appl. No.: 17/022,481

(22) Filed: Sep. 16, 2020

(65) Prior Publication Data
US 2021/0093286 A1  Apr. 1, 2021

(30) Foreign Application Priority Data
Sep. 26, 2019 (EP) .................................. 19199855

(51) Int. Cl.
*A61B 6/00* (2006.01)
*A61B 6/03* (2006.01)
*G06T 11/00* (2006.01)

(52) U.S. Cl.
CPC .............. *A61B 6/585* (2013.01); *A61B 6/032* (2013.01); *A61B 6/4241* (2013.01); *A61B 6/583* (2013.01); *G06T 11/005* (2013.01); *G06T 11/008* (2013.01)

(58) Field of Classification Search
CPC ....... A61B 6/585; A61B 6/032; A61B 6/4241; A61B 6/583; G06T 11/005; G06T 11/008; G01T 1/24; G01T 7/005
See application file for complete search history.

(56) References Cited

U.S. PATENT DOCUMENTS

| | | | |
|---|---|---|---|
| 2008/0212734 | A1 | 9/2008 | Bauscher, et al. |
| 2016/0242725 | A1* | 8/2016 | Wang .................. A61B 6/4233 |
| 2017/0224299 | A1 | 8/2017 | Petchke et al. |

FOREIGN PATENT DOCUMENTS

WO  WO 2006094493 A2  9/2006

OTHER PUBLICATIONS

J. Cammin et al.:; "Compensation of nonlinear distortions in photoncounting spectral CT: deadtime loss, spectral response, and beam hardening effects"; Proceedings of SPIE; vol. 8313; pp. 83131T-83131 T-7; XP055084909; ISSN: 0277-786X; DOI: 10.1117/12.911217; 2012.

Kappler, S. et al.: "Quantum-counting CT in the regime of count-rate paralysis: introduction of the pile-up trigger method"; SPIE; vol. 7961; pp. 1-10; XP040556068; 2011.

(Continued)

*Primary Examiner* — Courtney D Thomas
(74) *Attorney, Agent, or Firm* — Harness, Dickey & Pierce, P.L.C.

(57) ABSTRACT

A method for correction of an input dataset is disclosed. In an embodiment, the method includes acquisition of an input dataset comprising at least one data error; determination of a correction function; creation of a corrected output dataset by application of the correction function to the input dataset; and outputting of the corrected output dataset. The correction function is embodied to bring about a reduction of at least two data errors that mutually influence one another in the input dataset.

20 Claims, 3 Drawing Sheets

(56) References Cited

OTHER PUBLICATIONS

Tkaczyk, J.E. et al.:; "Contrast-to-Noise of a Non-Ideal, Multi-bin, Photon Counting X-ray Detector"; SPIE; vol. 7961; XP040556163; 2011.
European Search Report for European Patent Application No. 19199855 dated Mar. 17, 2020.

* cited by examiner

DATA CORRECTION IN X-RAY IMAGING

PRIORITY STATEMENT

The present application hereby claims priority under 35 U.S.C. § 119 to European patent application number EP 19199855.8 filed Sep. 26, 2019, the entire contents of which are hereby incorporated herein by reference.

FIELD

Embodiments of the invention generally relate to data correction in X-ray imaging.

BACKGROUND

Direct-converting or also (photon)-counting detectors, which make possible a spectrally resolved or energy-selective imaging, are an innovative technology in the field of x-ray imaging, in particular computed tomography. Counting x-ray detectors do not use scintillators that initially convert x-ray photons into optical light, but rather a semiconductor that detects x-ray photons directly. Advantageously direct-converting detectors, as well as the location, also resolve the energy of an incident photon, in spectral computed tomography for example. In this case x-ray quanta falling on the detector surface are assigned according to their quantum energy to specific energy bands or bins, i.e. are classified energy-selectively and in each case the events per pixel per energy band are counted. Counting x-ray detectors are consequently suitable for simultaneous creation of at least two projection datasets, which differ in their x-ray quantum energy distribution while using only one x-ray source. There are typically two to four energy bands. The at least two projection datasets are each formed by all pixel signals of the detector within an energy band. The semiconductors cadmium telluride, cadmium zinc telluride or gallium arsenide are particularly suitable as detector materials for quantum-counting detectors or, in the case of a flat-panel detector, amorphous selenium or the like.

The threshold values of the energy bands are defined beforehand by the manufacturers and the electronics in the detector module are set accordingly. Either fixed, invariable threshold values can be preset or the threshold values can be selected as a function of or together with a desired scan protocol, for example for a head or thorax recording, by the user. This means that the threshold values, in order to optimize the medically relevant information content of an acquired recorded image, can be suitably adapted to the anticipated diagnosis or to the medical issue.

In particular with photon-counting x-ray detectors there is the problem of strong non-linearities arising from pile-up effects in the detector, which in their turn are influenced by spectral effects such as a beam hardening.

Pile-up describes the case in which at least two detector events occur at an x-ray detector within a period of time that is shorter than the resolution time for a duration or the duration of an electrical impulse, which is created by a single incident x-ray quantum. If the detection events lie very close to each other in time, the detection events will be combined into one impulse with added-up amplitudes according to their quantum energy (peak pile-up). If the detection events now take place at a longer time interval, although they can be detected as independent events, however at least the x-ray quanta occurring later in time will be acquired with quantum energy falsified toward higher values (tail pile-up). Consequently, with a pile-up a counting loss of detection events similar to that caused by dead time can result. Moreover a shift of the x-ray quantum spectrum toward higher quantum energies is brought about. Depending on the energy bins previously defined, detection events overlaid by pile-up can be grouped together into incorrect bins and thus the count rate of a number of projection datasets falsified. Pile-up effects depend very greatly on the count rate of a system, i.e. the higher the count rate, the greater is the influence of pile-up effects of higher order (overlaying of more than two detection events).

A beam hardening effect is a shifting of the effective energy of an x-ray toward a higher value on penetration of material. The reason for this is the energy dependence of the linear coefficient of x-ray attenuation. As the depth of penetration increases the average energy of the x-ray quanta thus increases, since x-ray quanta of lower energies are absorbed by preference. The relative share of low-energy x-ray quanta becomes ever smaller as the passage through the material increases. Thus, the greater the thickness of the material, the more strongly the hardening error manifests itself in the acquired detector signals.

Non-linearities as a result of pile-up and beam hardening both manifest themselves in a shift of the effective x-ray beam energy toward a higher value. This means that they cannot be readily separated.

SUMMARY

Previously this problem has been addressed iteratively, by repeated correction steps, i.e. first of all by a non-linearity correction, then a beam hardening correction, then a non-linearity correction and so forth being carried out, by which the problem can be resolved at least approximately. The inventors discovered that this procedure described was long-winded and processor-intensive however.

By contrast, at least one embodiment of the invention provides alternate methods/devices that allow a correction of errors to be carried out reliably, automatically and quickly on energy-selective measurement data. In particular at least one embodiment of the present invention, at the same time, provides an error correction for at least two data errors that mutually influence one another.

Embodiments of the invention are directed to a method for correction of an input dataset, by a corresponding computing unit, a corresponding computer program and a corresponding computer-readable data medium. Preferred and/or alternate advantageous embodiment variants are the subject matter of the claims.

The inventive way in which the embodiments are achieved is described below in relation to the claimed method and also in relation to the claimed facilities. Features, advantages or alternate forms of embodiment mentioned here are likewise also to be transferred to the other claimed subject matter and vice versa. In other words, claims forming the subject matter (which are directed to a method for example) can also be further developed with features that are described or claimed in conjunction with one of the facilities. The corresponding functional features are embodied in such cases by corresponding modules or units forming the subject matter.

The present invention relates in a first embodiment to a method for correction of an input dataset. The method comprises:

an acquisition of an input dataset comprising at least one data error;

a determination of a correction function;

a creation of a corrected output dataset by application of the correction function to the input dataset; and an output of the corrected output dataset.

At least one embodiment of the invention relates in a further aspect to a computing unit for correction of an input dataset having means for carrying out at least one embodiment of the inventive method. The computing unit comprises:

an interface configured to acquire an input dataset including at least one item of error data, a determination unit configured to determine a correction function, a correction unit configured to create a corrected output dataset by applying the correction function to the input dataset, and an interface configured to output the corrected output dataset.

A further embodiment of the present invention relates to an x-ray detector in the form of an energy-selective x-ray detector, comprising at least one embodiment of the inventive computing unit.

At least one embodiment of the invention further relates to a computer program with program code for carrying out the inventive method for correction of an input dataset when the computer program is executed on a computer.

At least one embodiment of the invention further relates to a computer-readable data medium with program code of a computer program for carrying out at least one embodiment of the inventive method for correction of an input dataset when the computer program is executed on a computer.

At least one embodiment of the invention further relates to a method for correction of an input dataset, comprising:

acquiring an input dataset including at least one data error;

determining a correction function;

creating a corrected output dataset by application of the correction function to the input dataset; and outputting the corrected output dataset, wherein the correction function is embodied to bring about a reduction of at least two data errors that mutually influence one another in the input dataset.

At least one embodiment of the invention further relates to a computing unit for correction of an input dataset, comprising:

an interface configured for acquisition of an input dataset comprising at least one data error;

a determination unit configured for determining a correction function;

a correction unit configured for creating a corrected output dataset by applying the correction function to the input dataset; and an interface configured for outputting the corrected output dataset, wherein the correction function is embodied to bring about a reduction of at least two data errors in the input dataset that mutually influence one another.

At least one embodiment of the invention further relates to an energy-selective x-ray detector, comprising the computing unit of claim 12.

At least one embodiment of the invention further relates to a non-transitory computer program, directly loadable into a memory unit of a computing unit, including program sections for carrying out the method of an embodiment when the computer program is executed in the computing unit.

At least one embodiment of the invention further relates to a non-transitory computer-readable medium, storing program sections readable in and executable by a computing unit, for carrying out the method of an embodiment when the program sections are executed by the computing unit.

BRIEF DESCRIPTION OF THE DRAWINGS

The characteristics, features, and advantages described above, as well as the manner in which these are achieved, will become clearer and easier to understand in conjunction with the description given below of the example embodiments, which are explained in greater detail in conjunction with the drawings. There is no restriction of the invention to these example embodiments by this description. In different figures the same components are provided with identical reference characters. The figures are not true-to-scale as a rule. In the figures.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The present invention relates in a first embodiment to a method for correction of an input dataset. The method comprises a plurality of steps.

A first step relates to an acquisition of an input dataset comprising at least one data error. A further step relates to a determination of a correction function. A further step relates to a creation of a corrected output dataset by application of the correction function to the input dataset. A further step relates to an output of the corrected output dataset.

At least one embodiment of the invention is characterized by the embodiment of the correction function, which brings about a reduction of at least two data errors that mutually influence one another in the input dataset. In other words, by means of the correction function proposed here, in parallel, i.e. in one processing step, two data errors that cause a falsification of the input dataset can be minimized or rectified.

The mutual influencing of the at least two data errors includes at least of the different data errors acting in a similar way as error effects on the input dataset, so that proportions of the data falsification can no longer be uniquely attributed to one of the two data errors.

At least one embodiment of the inventive method, using at least one embodiment of the inventive correction function, converts an input dataset into an output dataset. In other words the correction function corresponds to a set of mathematical rules, which transforms an input dataset into an output dataset.

While the input dataset has data errors, the output dataset is freed from these data errors. The data errors in the output dataset are at least greatly reduced.

The input dataset is characterized by comprising error effects at least based on one, preferably based on at least two different data errors.

At least one embodiment of an inventive input dataset corresponds to projection data of an x-ray detector, as arises in a medical examination of a patient, for example a computed tomography examination. In this respect the input dataset is in particular a medical input dataset. In particular the input dataset comprises at least two projection datasets, which differ spectrally, i.e. in their (average) x-ray quantum energies. A projection dataset in this case for the quantum energy spectrum imaged by it is representative for a spatial intensity distribution of incident x-ray quanta over the sensitive detector surface, wherein the detected x-ray quanta, starting from the x-ray source, have passed through an examination object. Each pixel entry, i.e. measured projection value of the projection dataset, consequently corresponds to a number of x-ray quanta that have arrived in this pixel with a quantum energy corresponding to the respective energy range, energy band or energy bin. The input dataset consequently corresponds to an error-prone, detected attenuation distribution of the imaged examination object.

In other words the step of acquiring the input dataset comprises a (medical) recording of measurement data via an x-ray source and x-ray detector as well as the transmission of the measurement data into a computing unit for further processing there.

An examination object in the sense of at least one embodiment of the invention is a patient, wherein this mostly involves human beings. Basically the patient can also be an animal. The examination object can however also be an inanimate, in particular a non-medical object, for example a pathological sample, a mechanical component but also a historical artifact. Therefore the two terms "examination object" and "patient" are used synonymously below.

At least one embodiment of an inventive output dataset corresponds to an input dataset from which the errors included in it have been cleared. That means that the output dataset is also embodied in particular as a medical output dataset, which is to be understood for example as a projection dataset of an x-ray detector, like the input dataset in particular can comprise at least two spectrally different projection measurement datasets. The output dataset consequently corresponds to a corrected, detected attenuation distribution of the imaged examination object.

The step of outputting the output dataset preferably comprises a transmission of the output dataset to a processing unit or reconstruction unit, which is configured, by means of a set of reconstruction rules known per se, such as for example an (iterative or weighted) filtered backprojection or an algebraic reconstruction, to create essentially artifact-free x-ray image data.

At least one embodiment of the inventive sequence of steps of the method is not defined by the sequence of steps listed here. In particular the step of determining the correction function can be preceded entirely or at least partly by the other steps.

In one embodiment of the inventive method, the correction function is embodied to at least reduce data errors in the input dataset based on a pile-up effect and beam hardening effect occurring during the acquisition of the input dataset. These two effects causing data errors already explained at the start mutually influence one another, since, inter alia, they each cause a shift of the detected x-ray quantum energy spectrum toward higher values, so that it can no longer be established what proportion of the data errors is attributable to which of the two effects. The inventive correction function advantageously renders superfluous an assignment of the proportion of data errors to the effects causing them and corrects these together, whereby computing time can be saved and work sequences made more effective.

In another embodiment of the inventive method, the correction function is further embodied to reduce a further data error based on a scattered radiation effect in the input dataset. The scattered radiation effect refers to the occurrence of scattered x-ray quanta, which change their direction of radiation on interaction with irradiated material. Scattered x-ray quanta, if at all, do not strike a corresponding detector pixel in their original radiation direction and in this way cause a falsification of the spatial x-ray intensity distribution. Above and beyond this x-ray quanta lose a part of their quantum energy through a scattering phenomenon, so that a scattered x-ray quantum can be assigned to an incorrect energy band. The scattered radiation intensity depends on the material thickness and also the type of the material. Scattered radiation can in particular comprise radiation arising from a multiple scattering, i.e. higher-order scattered radiation. Scattered radiation can further be embodied as transverse scattering of a dual-energy x-ray imaging system. In other words the scattered radiation corresponds to that radiation that is emitted by an x-ray source of a first emitter-detector pair, however is scattered so that it is detected by the x-ray detector of a second emitter-detector pair of the system and/or vice versa. The inventive correction function advantageously renders superfluous a further assignment of data error shares to the effects causing them and effectively corrects said errors together.

The embodiments of the inventive method now given below can be suitable alone or in combination for specifying a method for determining a correction function, wherein the inventive correction function brings about a reduction of at least two data errors that mutually influence one another in the input dataset.

In another embodiment of the inventive method, the correction function is embodied as a function dependent on a monitor value relating to the x-ray source used for the acquisition of the input dataset. The monitor value is embodied to specify a measure for the applied x-ray radiation. The monitor value is preferably embodied as the x-ray tube current set at the x-ray source, which decisively defines the intensity of the x-ray bundle emitted by means of x-ray tubes. The monitor value can also be a dose value. In other words the correction function is embodied to carry out an x-ray current or x-ray intensity-dependent correction of the input dataset. This is especially advantageous since it takes account of the dependency of data errors on the intensity or the count rate.

In another embodiment of the inventive method, a determination of the correction function comprises a calibration measurement with a spectrally resolving x-ray detector.

A spectrally resolving x-ray detector is embodied to create a measurement dataset that comprises at least two spectrally differing projection datasets. In other words a spectrally resolving x-ray detector is an energy-selective x-ray detector. A spectrally resolving x-ray detector can be embodied as a quantum-counting x-ray detector, as already described at the outset. However it can also be embodied as a two-layer detector.

A two-layer detector or also dual or double layer detector is embodied to break down the incident x-ray tube spectrum into a low-energy and a high-energy portion. To this end the two-layer detector is constructed from two layers. A detector layer facing toward the x-ray source measures x-ray photons of the incident x-ray radiation with low energy and allocates the measured signals to a first projection measurement dataset. This first detector layer is penetrated by high-energy x-ray radiation. X-ray photons with higher quantum energy will be measured in the detector layer below or behind it, i.e. facing away from the x-ray source and assigned to a second projection measurement dataset. Typically both detector layers comprise a scintillator, consequently a two-layer detector typically involves an indirect-converting detector. Crystals such as cesium iodide, cadmium tungstenate or ceramic substances, such as for example gadolinium oxysulfide or the like are used a scintillation material.

In other words in this embodiment spectrally resolved calibration data comprising at least two spectrally different calibration datasets is created, which is included in the determination of the correction function.

In a preferred embodiment of the inventive method, the calibration measurement comprises an acquisition of calibration data of a test object comprising at least two base materials. In other words in this embodiment a calibration dataset comprising at least two spectrally different calibration datasets is created, of which each describes an x-ray attenuation distribution of the test object in relation to its energy bin. The test object, essentially a phantom, is made of at least two base materials. As an alternative the test object can be made of two test objects each comprising just one base material.

Thus the calibration data is advantageously suitable for a base material decomposition.

In a base material decomposition the starting point is the idea that an x-ray attenuation value measured by means of x-ray detectors can be described as a linear combination or line integral along a radiation path of x-ray attenuation values of the base materials in relation to the x-ray quantum energy distribution of each energy band. Measured x-ray attenuation values or distributions are produced from at least two calibration datasets for different x-ray quantum energy distributions in each case. Material or base material can be any substance or any given tissue, in particular water, contrast media such as iodine, soft tissue, bones and the like can be considered. More than two base materials can also be combined within the framework of the invention.

In this respect the base materials, in a preferred embodiment of the inventive method, comprise one of the following material combinations:

Water-iodine,
Water-bone, or
Aluminum-iron.

At least one embodiment of the inventive calibration measurement advantageously comprises a number of measurements with a number of test objects, which differ in the thickness of the base materials that they comprise. For example a number of test objects can be measured with one material combination, for example water and bone, wherein the thickness of one of the base materials increases further and the thickness of the second base material also increases or decreases to the same extent.

For each thickness ratio of the material combination moreover a number of measurements with a different monitor value, in particular a different tube current of the x-ray source, are carried out.

In this way a series of calibration datasets are created for the selected material combination and different thickness ratios of the materials, which represent an energy, thickness and x-ray tube-dependent x-ray attenuation distribution of the base materials. In other words, for calibration dataset pairs/groups each comprising two calibration datasets from two or more energy bands of the x-ray detector, a base material decomposition can be carried out.

The x-ray attenuation behavior of a base material is known in theory and is available for example in the form of tables for retrieval. In this respect, even for any given combination of base materials and any given thickness ratios of the same and different monitor values, an attenuation dataset to be expected, i.e. an ideal attenuation dataset, is known and able to be determined.

At least one embodiment of the present invention is now based on the idea that the calibration data created as described in relation to the test object already has the data errors described and in consequence the calibration datasets deviate from the theoretically known or ideal x-ray attenuation behavior. In accordance with at least one embodiment of the invention, the correction function is now determined as that function depending on the monitor value that maps the calibration datasets onto the ideal projection datasets.

The correction function can be embodied as a polynomial, as a linear combination of a number of functions or as a non-linear function. A linear combination in particular has the advantage that the optimization is able to be carried out analytically mathematically very easily and directly, i.e. coefficients in this case are able to be calculated directly and not iteratively. Depending on the embodiment of the correction function a parameterization of the correction function is undertaken based on the calibration datasets and the ideal projection datasets.

In a further embodiment of the inventive method, the calibration measurement of a test object comprises at least two integrated cross sections of Compton effect and photo effect. This embodiment represents an alternative to the previous embodiment of the invention. Instead of breaking down an x-ray attenuation coefficient into individual attenuation coefficients of two or more base materials, it can also be broken down interaction-specifically into a Compton attenuation coefficient and a photo attenuation coefficient, which can be established in a similar way to base material decomposition by inversion of two spectrally different calibration datasets. The theoretical/ideal attenuation coefficients are known for different materials and different monitor values. The test object in this embodiment can also comprise just one material. In the Compton effect, an x-ray quantum in an elastic collision with an electron emits a part of its kinetic energy while changing direction. In the photo effect the x-ray quantum is completely absorbed by the electron.

In a further embodiment of the inventive method, the determination of the correction function comprises a calibration measurement of a test object taking into consideration at least two monochromatic cross sections. This embodiment represents a further alternative to the previous embodiments of the invention. Instead of breaking down an x-ray attenuation coefficient into individual attenuation coefficients of two or more base materials, it can also be broken down energy-selectively into attenuation coefficients for specific quantum energy values n, which are likewise able to be established by inversion of two spectrally different calibration datasets. The theoretical/ideal attenuation coefficients are again known for different materials and different monitor values. In this embodiment too the test object can comprise just one material.

In a further, alternate embodiment of the invention, a determination of the correction function comprises a simulation of a calibration measurement in one of the embodiments described above. Here the calibration datasets, that is to say measured calibration values of each pixel element of the x-ray detector, are established purely computationally, in that by means of a simulation specification the detection behavior for each individual energy band of each individual detector pixel is simulated depending on the monitor value for a defined test object. The simulation preferably generates data errors in the simulated measured calibration values, as are caused by pile-up effects or a beam hardening. Especially preferably the simulation additionally generates a data error, as would be brought about by scattered radiation.

In a further embodiment of the inventive method, the correction function is embodied as a function trained by machine learning. Machine learning in the sense of the invention comprises a computer-implemented technique, in which an algorithm recognizes patterns or regularities on the basis of existing data and using the same obtains its own solutions independently in relation to unknown new data. The requirement for finding a solution independently is a training phase, in which an algorithm of machine learning is applied to a known, defined and mostly very large amount of data, in order to find those rules or predictions that obtain a desired output or a desired result. The training can be embodied as supervised or unsupervised, wherein in the first variant the algorithm is presented with pairs of values in the form of input values and correct output values belonging to them, while in the second variant the algorithm, based on the input values, must independently adapt them itself in such a way that it delivers correct output values.

Especially advantageously the algorithm of the machine learning is embodied as an artificial neural network. An artificial neural network, between an input and an output layer, preferably comprises a plurality of further layers each comprising at least one node. Each node corresponds in this case to a processing unit. Nodes within a layer of the network can be connected via directed connections (edges) to nodes of other layers. The connections define the flow of data within the network. Each node consequently represents an operation that is applied to the input data. Each node or each of its connections further has a weighting parameter (weight). Via this weight the influence or the importance of the output of a node is defined as an input value for a receiver node. In the training phase, which is preferably carried out as supervised learning, the artificial neural network 'learns' on the basis of the training data the weights for all nodes or connections and adapts these until such time as the output layer of the network is delivering the correct output values.

A trained function of machine learning thus, within the framework of its training, establishes a fixed connection between input values, here in the form of the calibration datasets and monitor values belonging thereto, and output values in the form of ideal projection datasets. The trained function in this embodiment replaces the correction function.

At least one embodiment of the invention relates in a further aspect to a computing unit for correction of an input dataset having means for carrying out at least one embodiment of the inventive method. The computing unit comprises:

an interface configured to acquire an input dataset including at least one item of error data, a determination unit configured to determine a correction function, a correction unit configured to create a corrected output dataset by applying the correction function to the input dataset, and an interface configured to output the corrected output dataset.

The correction function is embodied to bring about a reduction in the input dataset of at least two data errors that mutually influence one another.

The computing unit can be embodied in particular as a computing unit of a medical imaging system, comprising an x-ray source, an energy-selective x-ray detector and a patient couch. The computing unit can also be embodied as the computing unit of an energy-selective x-ray detector. In a preferred embodiment the computing unit is connected to the medical imaging system comprising the energy-selective x-ray detector. As an alternative the computing unit is connected to the energy-selective x-ray detector directly. Advantageously the computing unit is integrated into the medical imaging system. As an alternative the computing unit can also be arranged remotely or at distance therefrom. The computing unit can be embodied in particular to carry out the step of determining the correction function, but also the entire inventive method of at least one embodiment, for a medical imaging system or for a plurality of systems, e.g. in a radiology center or hospital comprising a number of medical imaging systems.

A further embodiment of the present invention relates to an x-ray detector in the form of an energy-selective x-ray detector, comprising at least one embodiment of the inventive computing unit.

At least one embodiment of the invention further relates to a computer program with program code for carrying out the inventive method for correction of an input dataset when the computer program is executed on a computer.

At least one embodiment of the invention further relates to a computer-readable data medium with program code of a computer program for carrying out at least one embodiment of the inventive method for correction of an input dataset when the computer program is executed on a computer.

Figure 1:
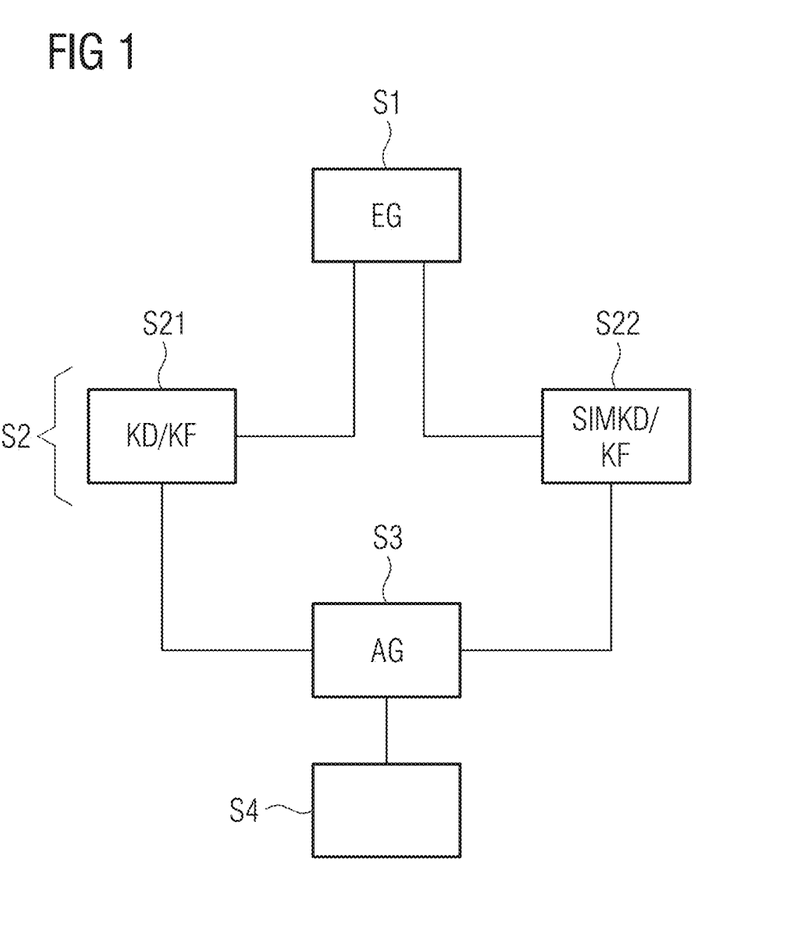
FIG. 1 shows a schematic diagram of the inventive method in an example embodiment of the present invention.

FIG. 1 shows a schematic diagram of the inventive method in an example embodiment. In a first step S1 there is an acquisition of medical input data or of a medical input dataset EG. The acquisition can comprise an acquisition of data with an imaging system, in particular comprising an x-ray detector 9 in accordance with FIG. 3 or 4. In other words the acquisition in accordance with step S1 can comprise the creation or the generation of the medical input dataset EG. As an alternative the medical input dataset EG can be a dataset already acquired and existing, which can be read out from an external or internal memory unit 22, for example from a hospital information system comprising electronic patient files. The acquisition of the medical input dataset can generally also comprise an acquisition of the input dataset EG by means of interface 31 or data processing unit 16 or correction unit 23 of the imaging system 1, i.e. can comprise the step of transmission or reading in of the input data from one of the said data sources 9, 22, etc. In general the step S1 of acquisition comprises the procurement of the input dataset EG.

The acquisition in accordance with step S1 can also comprise an acquisition of those monitor values m relating to the x-ray source 8 that was set for the acquisition of the input dataset EG at the x-ray source 8. The monitor value m can be included for example as meta information in the input dataset EG itself and be transmitted along with said information. As an alternative the monitor value m can be stored (buffered) and transmitted as a self-contained variable, however comprising a relation or link to the input dataset EG. The monitor value m in accordance with the invention represents a measure for the applied x-ray radiation. In this example embodiment it corresponds to the tube current of the x-ray source 8. It can however also correspond to an x-ray dose value.

The medical input dataset involves projection data, as can be acquired with an x-ray detector 9 for example. The projection data describes a spatial distribution of the radiation intensity of an x-ray bundle that, starting from an x-ray source, has passed through an examination object and in doing so, depending on the nature, composition and thickness of the tissue passed through, has been attenuated. In order to resolve the spatial x-ray distribution, the x-ray detector, for a plurality of pixel elements arranged in a planar arrangement, acquires the number of incident x-ray quanta in this pixel element. The projection data results in accordance with the invention from an x-ray measurement with an energy-selective x-ray detector, for example in the form of a two-layer detector or a quantum-counting detector. Energy-selective detectors are embodied, for each pixel element, to deliver two or more than two energy-selective measured values. Incident x-ray quanta are classified according to their quantum energy in one of the energy ranges set in advance. A projection dataset comprises the totality of all measured pixel values of an energy range. The projection data of the input dataset can thus comprise one, two or more projection datasets corresponding to the number of energy ranges. Where a data acquisition makes provision for an examination of the examination object in a number of projection directions, the projection data can comprise a number of projection datasets in relation to each energy range corresponding to the number of projection directions.

The medical input dataset EG includes data errors. The data errors stem from at least the two imaging errors pile-up and beam hardening. The medical input dataset EG can moreover also have data errors in the form of scattered radiation errors. What is common to all data errors is that they mutually influence one another, so that a separation of the data error shares corresponding to the effects causing them is not possible or is only possible with much computing effort.

In a second step S2 there is the determination of a correction function KF. The correction function KF is determined in such a way that it is configured to correct the said data errors in the input dataset EG. The correction function KF is further embodied as a function dependent on the monitor value m. Step S2 is preferably carried out by a determination unit 21 of a computing unit 12. Step S2 can be carried out before or after step S1. Step S2 can be embodied as one or more alternate forms of embodiment S21, S22. In accordance with step S21 the correction function is determined via a calibration measurement of a test object. In accordance with step S22 the correction function is determined via a simulation of a calibration measurement. Especially preferably the determination of the correction function comprises training a machine learning algorithm.

Step S21 comprises a calibration measurement with a spectrally resolving x-ray detector 9. The calibration measurement is carried out with a test object comprising two base materials, alternatively also more base materials, for example if materials with K-edge absorption are to be quantified. The following base material combinations are preferred:

Water-iodine,
Water-bone,
Aluminum-iron.

A test object with a selected base material combination is measured for a plurality of different thickness ratios, for example in the following ratios:

| Thickness of material 1 (cm) | Thickness of material 2 (cm) |
|---|---|
| 0 | 1/2/3 |
| 5 | 0/1/2/3 |
| 10 | 0/1/2/3 |
| 20 | 0/1/2/3 | and/or

| Thickness of material 2 (cm) | Thickness of material 1 (cm) |
|---|---|
| 0 | 5/10/20 |
| 1 | 0/5/10/20 |

-continued

| Thickness of material 2 (cm) | Thickness of material 1 (cm) |
|---|---|
| 2 | 0/5/10/20 |
| 3 | 0/5/10/20 |

The test object can be composed of test objects comprising just one base material of a specific thickness in each case.

The calibration measurement can be carried out for a plurality of monitor values m. The result of the calibration measurement is calibration data KD comprising a plurality of calibration datasets for a plurality of thickness ratios. Each calibration dataset comprises measured calibration values $s_i=[s_1, \ldots, s_x]$ for each pixel element, which are specific in each case for one of the energy ranges of the x-ray detector. For each monitor value m and each thickness ratio at least two spectrally different calibration datasets corresponding to the energy ranges of the x-ray detector are present.

An embodiment of the invention is now based on the idea that the measured calibration values $s_i$ for each pixel element are just as prone to error effects such as pile-up, beam hardening etc. as measured values of projection datasets. However the ideal, energy-dependent attenuation behavior is known for base materials. Thus, for each thickness ratio of a base material combination, ideal attenuation datasets $j_i=[j_1, \ldots, j_x]$ are known or can be computed for all possible tube currents m.

An embodiment of the invention now uses the generally known assumption that a measured (x-ray attenuation) measured value into which the attenuation proportions of base materials causing x-ray attenuation can be broken down and uses the fact that for all constellations of monitor value-base material composition/thickness ratio at least two spectrally different calibration datasets are present for the x-ray detector.

For each calibration dataset of the calibration data a base material decomposition is now carried out for each measured calibration value, i.e. for each pixel element. In other words each measured calibration value $s_i$ will be represented as a function of the base material line integrals $L=[L_1, \ldots, L_p]$, $p \leq n$, n=number of base materials, to $s_i=[m, L_1, \ldots, L_p]$.

The ideal measured attenuation values $j_i$ can also be represented as a function of the base material line integrals L to $j_i=[m, L_1, \ldots, L_p]$.

The correction function KF is now determined for each energy range so that for each energy range the measured calibration values $s_i$ and the monitor value m are mapped to the (ideal) line integrals to $L=KF(s, m)$.

In one embodiment, the correction function KF can be a polynomial in the variables $s_i$ and m, which reflects the relationship between the variables s, m and L in the optimum way. As an alternative the correction function Kf can also be shown as a linear combination of other functions in $s_i$ and m.

In both cases the problem, formulated as a least squares problem, leads to a linear equation system. As an alternative the correction function could also be embodied as a non-linear function and be adapted in such a way that it reflects the measured calibration values in the optimal way.

Instead of the measured calibration values $s_i$ first of all the logarithmic variables could be computed for $L:=-\log(sim)+\log(si0m0)$, wherein the variables identified with index 0 are the measured calibration values obtained in a calibration measurement of the x-ray detector (e.g. free air, i.e. without test object). The advantage of this method is that after a renewed calibration measurement the operating point of the correction function KF is re-established, so that for example an air calibration measurement with the air calibration current would certainly have the value $\tilde{L}:=0$ as input value for the correction function KF.

Instead of the logarithmic variable $\tilde{L}$ the de-logarithmized variables $1:=sim/si0m0$ could also be used with the same effect in the input of the correction function KF. As an alternative the de-logarithmized variables $1_a:=\exp(-L_a)$: $a=1, \ldots, p.$ could be used in the output of the correction function KF.

Figure 2:
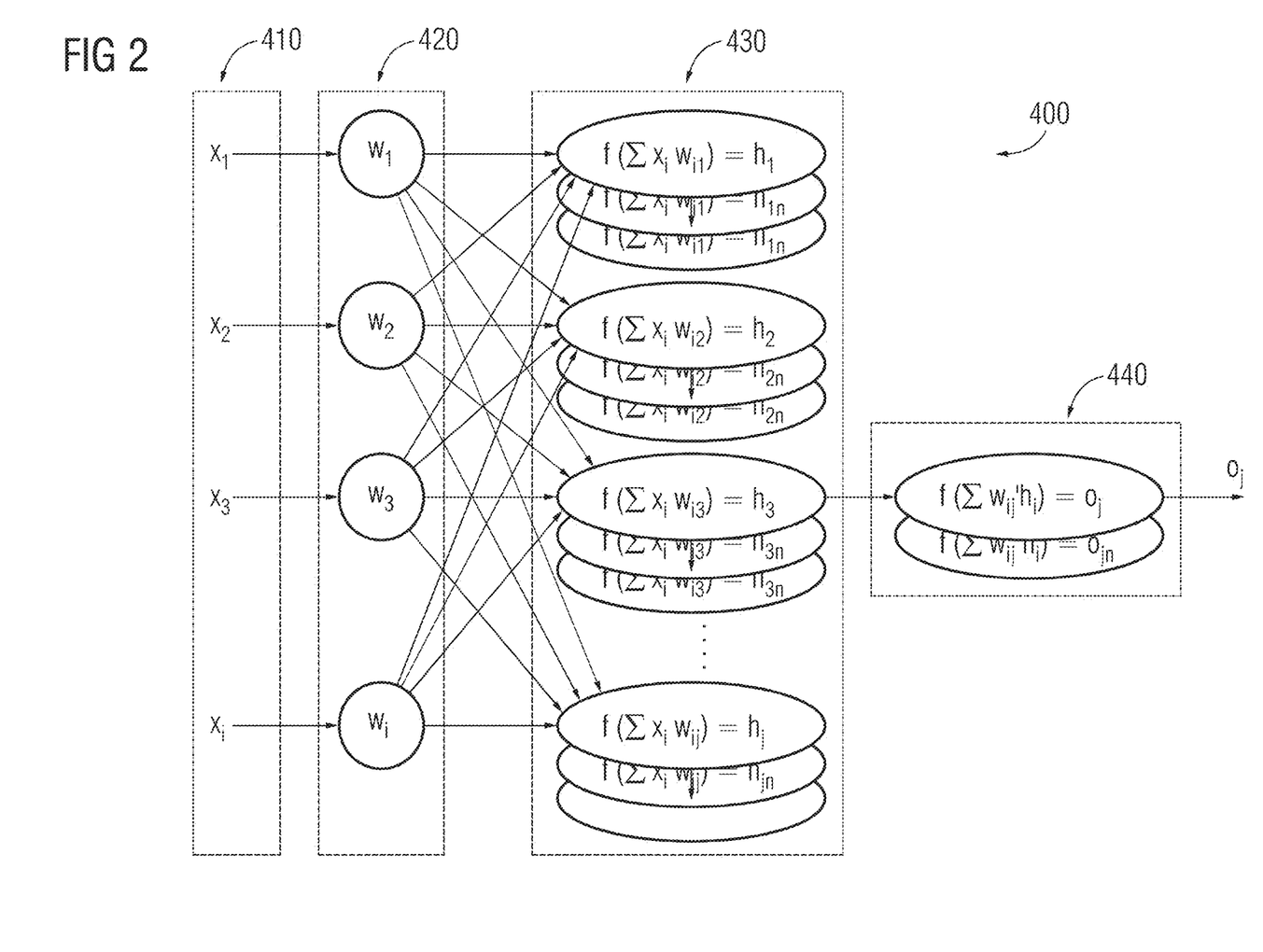
FIG. 2 shows a schematic diagram of a neural network for use in an embodiment of the inventive method.

In another embodiment, the correction function KF can be embodied as a function trained by means of machine learning, in particular as a neural network 400. The measured calibration values $s_i$ as well as the monitor values m in this embodiment can be used as training input data. The alternate embodiments of the measured calibration values (logarithmized or de-logarithmized) might possibly make it easier for the correction function KF to learn through the neural network 400. The trained neural network could output the line integrals L, but also directly the ideal measured attenuation values $j_i$ as output values in accordance with the invention.

Instead of a base material decomposition, to determine the correction function KF, a calibration measurement of a test object can comprise taking account of at least two integrated cross sections of Compton effect and photo effect. This method of operation is based on the assumption that x-ray attenuations of all materials can be represented as a linear combination of the cross sections of photo effect (absorption effect) and Compton effect (scattering effect). This applies at least approximately in the absence of K-edge absorption. Similarly polychromatic x-ray attenuation distributions could also be represented as a linear combination of different monochromatic cross sections.

In an alternate step S22 simulated calibration datasets SIMKD are created by a simulation of a calibration measurement by means of x-ray detectors. Here the calibration data acquisition of the x-ray detector in the different constellations of base material composition and thickness ratio and monitor value described in relation to step S21 is simulated. In this case a scattered quantum flow Φ with a known spectrum could additionally be included in the simulation and the measured calibration values si could also be simulated as a function of the scattered quantum flow. Then the correction function KF, as a further input parameter, would have the scattered quantum flow Φ. Advantageously the correction function in this way could take account of data errors based on scattered radiation (which in turn changes the spectral or pile-up ratios of the x-ray detector).

A correction function KF in the form of a neural network would then have to be trained with different values of Φ.

In a step S3 the input dataset EG is corrected by applying the correction function KF to said dataset. Step S3 can preferably be carried out by a correction unit 23 of a computing unit 12. Through this the output dataset AG is created. The correction function frees the medical input dataset from the data errors contained therein or reduces them by correction of each individual measured projection value.

In a further preferred embodiment of the method, step S3 can comprise a test step to test for the presence of metals in the beam path that very greatly attenuate the x-ray radiation. In this situation the correction function KF could deliver unusable values. For this an x-ray image could initially be reconstructed from the uncorrected input dataset EG. On the basis of the x-ray image a metal detection known per se could be carried out. Detected metal portions of the image could be projected forward. From this information would be produced that contains the metal measurement beam. This additional information could preferably be incorporated into the correction function KF.

In a further step S4 the corrected output dataset AG is output to a reconstruction unit 32 for example for reconstruction of essentially artifact-free x-ray images.

FIG. 2 shows a correction function embodied as an artificial neural network 400, as can be used in the method in accordance with FIG. 1. The neural network 400 responds to input values at a plurality of input nodes $x_i$ 410, which are applied to create one or a plurality of outputs $o_j$. The neural network 400 learns in this example embodiment by adapting the weighting factors $w_i$ (weights) of the individual nodes based on training data. Possible input values of the input nodes $x_i$ 410 are the plurality of error-prone, energy-selective, x-ray current-dependent measured calibration values $s_i$ caused by pile-up, beam hardening, scattered radiation, etc. in relation to a test object and the tube current value m associated therewith. The output values 440 of the neural network 400 preferably correspond to the corresponding ideal measured attenuation data $j_i$ without the data errors caused by imaging errors or the line integrals L. The output 440 can be produced via a single or a plurality of output nodes $o_j$. The input values can be entered consecutively for example for each tube current value m such that each input node $x_i$ 410 receives the measured value of a detector pixel corresponding to the projection datasets. Accordingly the corrected projection datasets can be output pixel-by-pixel for each output node.

The artificial neural network 400 preferably comprises a hidden layer 430, which comprises a plurality of nodes $h_j$. A number of hidden layers $h_{jn}$ can be provided, wherein a hidden layer 430 uses output values of another hidden layer 430 as input values. The nodes of a hidden layer 430 perform mathematical operations. An output value of a node $h_j$ corresponds in this case to a non-linear function f of its input values $x_i$ and the weights $w_i$. After the receipt of input values $x_i$, a node $h_j$ carries out a summation of a multiplication weighted with the weights $w_i$ of each input value $x_i$ as determined by the following function:

$$h_j = f(\Sigma_i x_i \cdot w_{ij})$$

In particular an output value of a node $h_j$ is formed as a function f of a node activation, for example a sigmoidal function or a linear ramp function. The output values $h_j$ are transmitted to the output node or nodes $o_j$. A summation of a weighted multiplication of each output value $h_j$ is computed once again as a function of the node activation f:

$$o_j = f(\Sigma_i h_i \cdot w'_{ij})$$

The neural network 400 shown here is a feed-forward network in which all nodes 430 process the output values of a previous layer in the form of its weighted sum as input values. It goes without saying that in accordance with the invention other neural network types can be used, for example feedback networks, in which an input value of a node h can at the same time also be its output value.

The neural network 400 is trained to detect patterns by means of a supervised learning method. A known method of operation is backpropagation, which can be applied to all example embodiments of the invention. During the training the neural network 400 is applied to training input values and must create corresponding, previously known training output values. Training input values in accordance with the invention are the calibration datasets preferably relating to a plurality of test objects, of which the theoretical x-ray attenuation behavior is known. Training output values are the corresponding, ideal measured projection datasets, which for example can be retrieved from a training database as required. Mean square errors (MSE) between computed and expected output values are computed iteratively and individual weights 420 adapted until such time as the discrepancy between computed and expected output values lies below a predetermined threshold.

Figure 3:
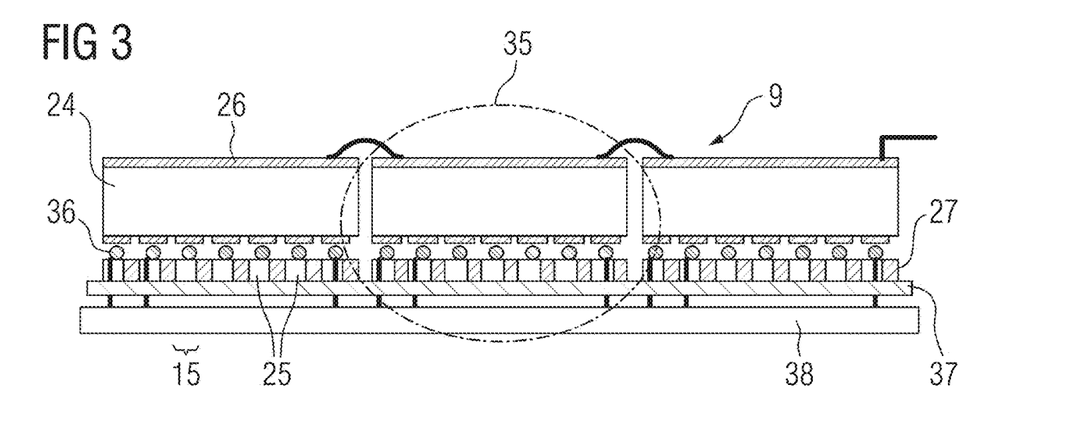
FIG. 3 shows an inventive x-ray detector in accordance with an example embodiment of the present invention.

FIG. 3 shows the schematic structure of a counting or direct-converting x-ray detector 9 in an example embodiment. This includes of a plurality of detector modules 35. A detector module 35 comprises a plurality of pixel elements 15, an ASIC 27, a section of a direct-converting material or direct converter 24 and a coupling between direct converter 24 and ASIC 27 (for example bump bonds 36). The ASIC 27 is connected via a substrate 37 to peripheral electronics 38. Incident x-ray radiation is converted in the direct converter 24 (for example CdTe or CZT) and the created charge carrier pairs are separated via an electrical field, which is created by a common top electrode 26 and a pixel electrode 25 specific for each pixel element 15. The charge creates a charge pulse in one of the pixel electrodes 25 of the ASIC 27, the height of which corresponds to the x-ray quantum energy. Thus in a pixel element 125 an event is counted by a digital memory unit being incremented by one. If the created electrical signal lies above at least one threshold value that can be set, the memory unit of the energy band lying above it is incremented, otherwise the memory unit of the energy band lying below it is incremented. The x-ray quanta counted in a specific energy range or energy band can be obtained by differentiating the counter contents of two corresponding counters. A threshold value is determined by means of discriminators. The threshold value can in principle on the one hand be predetermined as a fixed analog value, but is generally set up via a digital-to-analog converter (DAC) and is thus able to be adjusted variably in a certain range. Basically a threshold value can be set pixel-by-pixel or globally for all pixel elements 15. An embodiment of the inventive x-ray detector has at least one global threshold value.

Figure 4:
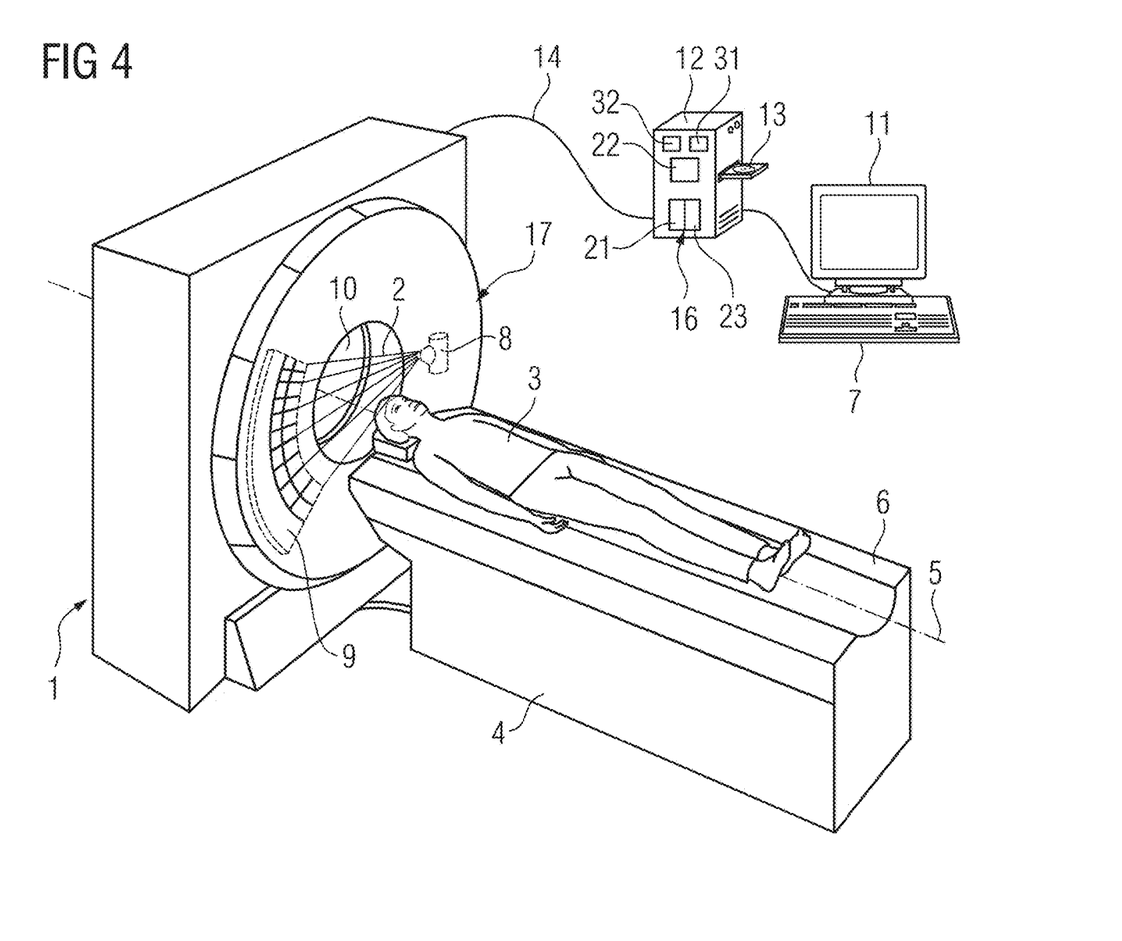
FIG. 4 shows a medical imaging system in the form of a computed tomography apparatus comprising an inventive computing unit in accordance with an example embodiment of the present invention.

FIG. 4 shows a medical imaging system 1 in the form of a computed tomography apparatus 1. Other x-ray imaging systems are likewise conceivable. The imaging system 1 is embodied to carry out the inventive correction method. In particular the imaging system 1 is embodied to create a medical input dataset EG and a medical output dataset AG. The imaging system 1 is further embodied to determine an inventive correction function KF.

The computed tomography apparatus 1 has a recording unit 17, comprising an x-ray (radiation) source 8 as well as an energy-selective x-ray (radiation) detector 9. The x-ray detector 9 is embodied as a direct-converting x-ray detector 9 and is essentially embodied for example in such a way as is described in relation to FIG. 3. Other embodiments are likewise conceivable. The recording unit 17 rotates during the recording of spectrally separated x-ray projections about a system axis 5, and the x-ray source 8 emits x-rays 2 during the recording, these pass through the patient 3 and in doing so are attenuated and strike the x-ray detector 9 as projection data.

The patient 3 lies during the recording of the spectrally separated x-ray projection data on a patient couch 6. The patient couch 6 is connected to a couch pedestal 4 so that it supports the patient couch 6 with the patient 3. The patient couch 6 is designed to move the patient 3 in a direction of recording through the opening 10 of the recording unit 17. The direction of recording is generally given by the system axis 5 about which the recording unit 17 rotates during the recording of the x-ray projection data. In this example the axis of the patient's body 3 is the same as the system axis 5. In a spiral recording the patient couch 6 is moved continuously through the opening 10 while the recording unit 17 rotates about the patient 3 and records x-ray projections. Thus the x-rays 2 describe a spiral on the surface of the patient 3. The patient 3 can but does not have to be moved during the examination.

The computed tomography apparatus 1 has a computing unit 12 in the form of a computer, which is connected to a display unit 11, for example for graphic display of medical image recordings, here in the form of computed tomography recordings or a control menu for the imaging system 1, as well as an input unit 7 for input of control commands for example.

The computing unit 12 is connected to the rotatable recording unit 17 via an interface 31 for exchange of data. On the other hand projection data recorded as medical input data for the patient 3 for the inventive method or an image reconstruction performed by means of usual reconstruction methods can be transmitted to the computer 12. The connection 14 is realized in the known way as a wired or wireless connection.

The computing unit 12 in the form of the computer in accordance with this example embodiment comprises a data processing unit 16.

The data processing unit 16 comprises means for executing steps of the inventive method. The data processing unit 16 consequently comprises a determination unit 21 for determining a correction function KF. In addition the data processing unit 16 also comprises a correction unit 23, which is configured to apply the correction function KF to the medical input dataset EG. Both units 21 and 23 can be embodied as separate processing units, but can also be embodied jointly in one unit. In the first case the units 21 and 23 at least have a data connection with one another, which can correspond to a network connection 14, in order to transmit the correction function KF established by the unit 21 to the unit 23 for application.

The computing unit 12 can further comprise a reconstruction unit 32, which receives output data AG corrected for the data errors from the correction unit 23 and by applying a reconstruction method known per se, creates medical image data of the patient 3. The reconstruction unit 32 can also be embodied as a sub-component of the data processing unit 16. In any event a data connection exists between correction unit 23 and reconstruction unit 32 in the form of a network connection 14.

The interface 31 can be embodied as a hardware or software interface, for example as a PCI bus, USB or Firewire. Data is preferably exchanged by means of a network connection 14. The network can be embodied as a local area network (LAN), for example an intranet or a wide area network (WAN). The network connection 14 is preferably embodied wirelessly, for example as a wireless LAN (WLAN or WiFi). The network can comprise a combination of different examples of networks. Data can be transmitted based on a data request or on one's own initiative. Data can be transmitted between two units or system components bidirectionally or unidirectionally.

The determination unit 21 can exchange data with an external (not shown) or internal memory unit 22, for example in order to retrieve tables relating to ideal attenuation data regarding base material combinations, photo and Compton cross sections or monochromatic cross sections. The external memory unit can be a hospital or radiology information system server (HIS or RIS) for example or a cloud storage facility which, in a way known per se, conveys for example table entries to the computing unit 12, in particular automatically, or provides them on request.

The computing unit 12 can interoperate with a computer-readable data medium 13, in particular to carry out an inventive method by a computer program with program code. Furthermore the computer program can be stored for retrieval on the machine-readable data medium. The machine-readable data medium can in particular involve a CD, DVD, Blu-Ray disk, a memory stick or a hard disk. The computing unit 12, and thus also its sub-components, can be embodied in the form of hardware or in the form of software. For example the computing unit 12 is embodied as a so-called FPGA (acronym for Field Programmable Gate Array) or comprise an arithmetic logic unit. The computing unit 12, individual or all of its sub-components can alternatively be arranged decentrally, e.g. individual computing steps of the method can be carried out in a central computer center of a medical service facility, e.g. a hospital, or in the cloud. Here in particular data and patient protection is to be taken into consideration in the exchange of data.

As a further alternative the computing unit 12 can be embodied as a sub-component of the x-ray detector 9 or as a (stand-alone) cloud-based computer, wherein the exchange of data with the imaging system 1 and/or the x-ray detector 9 is undertaken via a secure Internet connection. Communication occurs in a preferred example embodiment by DICOM standard, but other standards or data formats are likewise possible.

In the form of embodiment shown here at least one computer program is stored in a memory (22) of the computing unit 12, which carries out method steps of the inventive method when the computer program is executed on the computer 12. The computer program for carrying out method steps of the inventive method comprises program code. Furthermore the computer program can be embodied as an executable file and/or stored on a computer system other than the computer 12. For example the computed tomography apparatus 1 can be designed so that the computer 12 loads the computer program for executing the inventive method via an intranet or via the Internet into its internal random access memory.

In summary, the advantages of many embodiments of the present invention primarily lie in the fact that the correction of pile-up non-linearity and the correction of beam hardening no longer have to be corrected separately from one another. The inventive solution carries out both corrections and where necessary also the scattered radiation correction by means of correction functions tailored thereto in one correction step. Many calibration measurements and/or simulations are combined in order to parameterize the correction function or the correction algorithm. The inventive correction method results in error-cleared, corrected x-ray attenuation values, which can be included directly, i.e. without further pre-processing, in an image reconstruction. Since the x-ray attenuation values of a projection dataset are typically present for at least two energy channels, the corrected x-ray attenuation values are suitable for creating monochromatic images corresponding to a desired x-ray energy by means of linear combination.

Where this has not occurred explicitly but makes sense and is in the spirit of the invention, individual example embodiments, individual of their part aspects or features can be combined with one another or exchanged, without departing from the framework of the present invention. Advantages of the invention described in relation to one example embodiment, where they can be transferred, also apply, without this being explicitly stated, to other example embodiments.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method comprising:
   creating a corrected output dataset via an imaging modality, the input dataset including at least one data error;
   determining a correction function based on one or more characteristics of the imaging modality;
   creating a corrected output dataset by applying the correction function to the input dataset; and
   reconstructing an image based on the corrected output dataset, wherein
      the correction function is configured to reduce at least two data errors that mutually influence one another in the input dataset.

2. The method of claim 1, wherein
   the one or more characteristics of the imaging modality include at least one of a pile-up effect or a beam hardening effect, and
   the correction function is configured to reduce data errors in the input dataset based on the at least one of the pile-up effect or the beam hardening effect.

3. The method of claim 2, wherein
   the one or more characteristics of the imaging modality include a scattered radiation effect, and
   the correction function is configured to reduce data errors in the input dataset based on the scattered radiation effect.

4. The method of claim 1, wherein
   the one or more characteristics of the imaging modality include a scattered radiation effect, and
   the correction function is configured to reduce data errors in the input dataset based on the scattered radiation effect.

5. The method of claim 1, wherein
   the one or more characteristics of the imaging modality include a monitor value of an x-ray source used for acquiring the input dataset, and
   the correction function is dependent on the monitor value.

6. The method of claim 1, wherein the determining of the correction function includes acquiring a calibration measurement with a spectrally resolving x-ray detector.

7. The method of claim 6, wherein the calibration measurement includes calibration data of a test object including at least two base materials.

8. The method of claim 7, wherein the at least two base materials include at least one of the following material combinations:
   water and iodine,
   water and bone, or
   aluminum and iron.

9. The method of claim 6, wherein the calibration measurement includes calibration data of a test object, the calibration data including at least two integrated cross sections of Compton effect and photo effect.

10. The method of claim 6, wherein the calibration measurement includes calibration data of a test object, the calibration data including at least two monochromatic cross sections.

11. The method of claim 1, wherein the determining of the correction function includes simulating a calibration measurement.

12. The method of claim 1, wherein the correction function is a function trained by machine learning.

13. A non-transitory computer-readable medium, storing program sections that, when executed by a computing unit, cause the computing unit to carry out the method of claim 1.

14. A computing unit comprising:
   an interface configured to acquire an input dataset from an imaging modality, the input dataset including at least one data error;
   a determination unit configured to determine a correction function based on one or more characteristics of the imaging modality;
   a correction unit configured to create a corrected output dataset by applying the correction function to the input dataset; and
   a reconstruction unit configured to reconstruct an image based on the corrected output dataset, wherein
      the correction function is configured to reduce at least two data errors that mutually influence one another in the input dataset.

15. An energy-selective x-ray detector, comprising the computing unit of claim 14.

16. The computing unit of claim 14, wherein
   the one or more characteristics of the imaging modality include at least one of a pile-up effect or a beam hardening effect, and
   the correction function is configured to reduce data errors in the input dataset based on the at least one of the pile-up effect or the beam hardening effect.

17. The computing unit of claim 14, wherein
   the one or more characteristics of the imaging modality include a scattered radiation effect, and the correction function is configured to reduce data errors in the input dataset based on the scattered radiation effect.

18. The computing unit of claim 14, wherein
the one or more characteristics of the imaging modality include a monitor value of an x-ray source used for acquiring the input dataset, and
the correction function is dependent on the monitor value.

19. The computing unit of claim 14, wherein the determination unit is configured to determine the correction function by acquiring a calibration measurement with a spectrally resolving x-ray detector.

20. A device comprising:
one or more processors; and
a memory storing computer-executable instructions that, when executed by the one or more processors, cause the device to
acquire an input dataset via an imaging modality, the input dataset including at least one data error,
determine a correction function based on one or more characteristics of the imaging modality,
create a corrected output dataset by applying the correction function to the input dataset, and
reconstruct an image based on the corrected output dataset, wherein
the correction function is configured to reduce at least two data errors that mutually influence one another in the input dataset.

* * * * *